(12) United States Patent
Rivers et al.

(10) Patent No.: US 10,886,009 B2
(45) Date of Patent: Jan. 5, 2021

(54) INTEGRATED CONSOLE ENVIRONMENT FOR DIAGNOSTIC INSTRUMENTS METHODS AND APPARATUS

(71) Applicant: Beckman Coulter, Inc., Brea, CA (US)

(72) Inventors: Steven P. Rivers, Minneapolis, MN (US); Jeffrey J. Kotula, Eden Prairie, MN (US); Shilpa Taneja, Maple Grove, MN (US)

(73) Assignee: Beckman Coulter, Inc., Brea, CA (US)

( * ) Notice: Subject to any disclaimer, the term of this patent is extended or adjusted under 35 U.S.C. 154(b) by 941 days.

(21) Appl. No.: 14/844,334

(22) Filed: Sep. 3, 2015

(65) Prior Publication Data

US 2016/0070862 A1    Mar. 10, 2016

Related U.S. Application Data

(60) Provisional application No. 62/045,453, filed on Sep. 3, 2014.

(51) Int. Cl.
*G16H 10/40* (2018.01)
*G16H 10/60* (2018.01)

(52) U.S. Cl.
CPC ............. *G16H 10/40* (2018.01); *G16H 10/60* (2018.01)

(58) Field of Classification Search
CPC ......... G16H 10/40; G16H 10/60; G06F 19/00
See application file for complete search history.

(56) References Cited

U.S. PATENT DOCUMENTS

| | | | |
|---|---|---|---|
| 4,315,309 | A | 2/1982 | Coli |
| 8,069,239 | B2 | 11/2011 | Trochman |

(Continued)

FOREIGN PATENT DOCUMENTS

| | | |
|---|---|---|
| CN | 100426309 | 10/2008 |
| CN | 201716728 | 1/2011 |

(Continued)

OTHER PUBLICATIONS

Abaxis, Inc; Piccolo Xpress Chemistry Analyzer Operator's Manual, Sep. 2014, pp. 4-28 to 4-32, 3-9 to 3-12 (Year: 2014).*

(Continued)

*Primary Examiner* — Evangeline Barr
(74) *Attorney, Agent, or Firm* — Schwegman Lundberg & Woessner, P.A.

(57) ABSTRACT

A system, method, and apparatus for an integrated console environment for diagnostic instruments are disclosed. An example apparatus includes a laboratory analyzer configured to generate patient sample result data by performing an analysis on a biological sample from a patient and quality control data by performing an analysis on a control biological sample with known properties. The example apparatus also includes a first laboratory instrument memory configured to locally store the patient sample result data among a plurality of other patient sample result data and a first data access component at a first address configured to provide access to the first laboratory instrument memory. The example apparatus further includes a second laboratory instrument memory configured to locally store the quality control data among a plurality of other quality control data and a second data access component at a second address configured to provide access to the second laboratory instrument memory.

10 Claims, 6 Drawing Sheets

(56) References Cited

U.S. PATENT DOCUMENTS

| | | | |
|---|---|---|---|
| 2001/0004734 A1* | 6/2001 | Kudoh | G06Q 30/06 705/26.41 |
| 2002/0065686 A1 | 5/2002 | Monteleone et al. | |
| 2004/0220761 A1 | 11/2004 | Yundt-Pacheco | |
| 2005/0159982 A1 | 7/2005 | Showalter et al. | |
| 2008/0229037 A1* | 9/2008 | Bunte | G06F 11/1451 711/162 |
| 2008/0235055 A1 | 9/2008 | Mattingly et al. | |
| 2008/0307178 A1* | 12/2008 | Agombar | G06F 3/0605 711/162 |
| 2009/0150083 A1 | 6/2009 | Odachi | |
| 2010/0127885 A1* | 5/2010 | Okuno | G01N 33/48792 702/30 |
| 2011/0022343 A1 | 1/2011 | Cembrowski | |
| 2011/0157480 A1 | 6/2011 | Curl | |
| 2011/0172550 A1 | 7/2011 | Martin et al. | |
| 2012/0046203 A1 | 2/2012 | Walsh et al. | |
| 2012/0166094 A1 | 6/2012 | Parkhurst et al. | |
| 2012/0214159 A1* | 8/2012 | George | G06F 19/10 435/6.11 |
| 2013/0261611 A1 | 10/2013 | Dhar et al. | |
| 2014/0129172 A1 | 5/2014 | Eberhardt et al. | |
| 2015/0301002 A1* | 10/2015 | DeWitte | G01N 30/06 506/6 |
| 2015/0331946 A1* | 11/2015 | Balwani | G16H 10/40 707/769 |

FOREIGN PATENT DOCUMENTS

| | | |
|---|---|---|
| CN | 1735809 | 7/2014 |
| EP | 3189455 A1 | 7/2017 |
| JP | H09145716 A | 6/1997 |
| JP | 2002228667 A | 8/2002 |
| JP | 2002539561 A | 11/2002 |
| JP | 2007500573 A | 1/2007 |
| JP | 2007248088 A | 9/2007 |
| JP | 2007526799 A | 9/2007 |
| JP | 2007333700 A | 12/2007 |
| JP | 2010518488 A | 5/2010 |
| JP | 2013210937 A | 10/2013 |
| JP | 2014122889 A | 7/2014 |
| WO | WO-0055751 A1 | 9/2000 |
| WO | WO-2004104901 A1 | 12/2004 |
| WO | WO-2005072131 A2 | 8/2005 |
| WO | 2016/036968 A1 | 3/2016 |

OTHER PUBLICATIONS

International Search Report and Written Opinion dated Dec. 4, 2015 for International Application No. PCT/US2015/048385 filed on Sep. 3, 2015.

Abbot Diagnostics: "Cell-Dyn 1700 Operations Manual." Retrieved from the Internet: URL:http:www.blockscientific.com/manuals/cell-dyn-1700-operator-manual.pdf (1995).

Extended European Search Report for European Patent Application Serial No. 15837467.8 dated Apr. 5, 2018 (search completed on Mar. 23, 2018).

"European Application Serial No. 15837467.8, Communication Pursuant to Article 94(3) EPC dated Mar. 7, 2019", 14 pgs.

"European Application Serial No. 15837467.8, Response filed Oct. 12, 2017 to Communication Pursuant to Rules 161(2) and 162 EPC dated Apr. 12, 2017", 17 pgs.

"European Application Serial No. 15837467.8, Response filed Oct. 26, 2018 to Extended European Search Report dated Apr. 5, 2018", 22 pgs.

"International Application Serial No. PCT/US2015/048385, International Preliminary Report on Patentability dated Mar. 16, 2017", 11 pgs.

"Japanese Application Serial No. 2017-512297, Notification of Reasons for Rejection dated Jul. 1, 2019", w/ English Translation, 11 pgs.

"European Application Serial No. 15837467.8, Response filed Sep. 11, 2019 to Communication Pursuant to Article 94(3) EPC dated Mar. 7, 2019", 16 pgs.

"Chinese Application Serial No. 201580059868.1, Office Action dated Nov. 19, 2019", w/ English Translation, 45 pgs.

"Abbott Cell-Dyn 1700 System Operations Manual", Abbott Diagnostics, [Online] Retrieved from the Internet: <URL: https://www.blockscientific.com/manuals/cell-dyn-1700-operator-manual.pdf>, (Feb. 28, 1995), 19 pgs.

"Chinese Application Serial No. 201580059868.1, Response filed Mar. 27, 2020 to Office Action dated Nov. 19, 2019", w/ English claims, 57 pgs.

"European Application Serial No. 15837467.8, Summons to Attend Oral Proceedings mailed Feb. 11, 2020", 11 pgs.

"Japanese Application Serial No. 2017-512297, Response filed Jan. 6, 2020 to Notification of Reasons for Rejection dated Jul. 1, 2019", w/ English claims, 9 pgs.

"Chinese Application Serial No. 201580059868.1, Office Action dated Jun. 9, 2020", w English Translation, 42 pgs.

* cited by examiner

INTEGRATED CONSOLE ENVIRONMENT FOR DIAGNOSTIC INSTRUMENTS METHODS AND APPARATUS

PRIORITY CLAIM

The present application claims priority to and the benefit of U.S. Provisional Patent Application No. 62/045,453 filed on Sep. 3, 2014, the entirety of which is incorporated herein by reference.

BACKGROUND

In many known laboratory environments, laboratory instruments are connected to a data management center that includes a centralized server and/or centralized storage device. Generally, data generated by the laboratory instruments, such as test results of a biological sample, are transmitted to the data management center. One or more servers within the data management center manage the storage and access of substantially all the laboratory data. Such a configuration enables client devices across an enterprise and/or outside the enterprise to access the centrally stored data. Such a configuration also streamlines data management because the data is located in one centralized location.

The centralized approach to data storage has some known drawbacks. First, an outage or degradation in performance of a data management center affects data access across an entire enterprise. Some data management centers use backup or redundant servers and data storage devices to reduce the effects of an outage. However, there is oftentimes a disruption in access to data as the backup or redundant servers come online. Additionally, a spike in traffic resulting from the outage may cause the backup or redundant servers or data storage devices to also go offline. Losing access to critical laboratory data, even temporarily, is problematic, especially in hospital or medical environments.

A second issue with the centralized approach is that information technology departments have to provision servers and data storage devices to account for peak traffic times when many enterprise client devices may be accessing the same servers or data storage devices. To account for peak traffic, information technology departments oftentimes over provision servers and/or data storage devices to ensure there is enough bandwidth and processors available for peak system loads. However, over provisioning generally results in underutilized servers or data storage devices during non-peak times. Generally, these centralized systems are not scaled on a daily basis as a result of the inefficiencies that result from constantly activating (e.g., scaling) and deactivating servers or data storage devices.

A third issue with the centralized approach is that servers and data storage devices within a data management center have to be upgraded to account for any changes or upgrades to laboratory instruments. For instance, en enterprise may include tens to hundreds of laboratory instruments that transmit data to a centralized system. Each laboratory instrument may be configured with a specific data configuration, communication protocol, operating system, etc. such that any given enterprise may have to account for many different types and methods of receiving data. An update to the software of one instrument or the addition of a new instrument may introduce a new protocol or configuration that is not compatible with the current system. As a result, the entire centralized system may have to be updated when only one of tens or hundreds of lab instruments is updated or changed.

SUMMARY

The present disclosure provides a new and innovative system, method, and apparatus for implementing an integrated console environment for diagnostic laboratory instruments. In an example embodiment, a laboratory apparatus of an integrated console environment includes a laboratory analyzer configured to generate patient sample result data by performing an analysis on a biological sample from a patient and quality control data by performing an analysis on a control biological sample with known properties. The laboratory apparatus also includes a laboratory instrument memory configured to locally store the patient sample result data among a plurality of other patient sample result data and a laboratory processor configured to operate in conjunction with the laboratory analyzer to determine whether data generated by the laboratory analyzer is the patient sample result data or the quality control data. The laboratory processor is also configured to, conditioned on the generated data being the patient sample result data, store the patient sample result data to the laboratory instrument memory, and conditioned on the generated data being the quality control data, transmit the quality control data to a remotely located memory. The example laboratory processor is further configured to transmit, at a predetermined time from generation, the patient sample result data to the centrally located persistent memory.

In another example embodiment, an application server of an integrated console environment is configured to receive a request from a client device for patient sample result data, the request including an identifier of a patient associated with the patient sample result data and determine whether the patient sample result data is stored in a central memory communicatively coupled to the application server. The application server is also configured to, conditioned on the patient sample result data being stored in the central memory, read the patient sample result data from the central memory and transmit the patient sample result data to the client device. Moreover, the application server is configured to, conditioned on the patient sample result data not being stored in the central memory, broadcast a query message to a plurality of laboratory instruments requesting the patient sample result data, the query message including the identifier, responsive to the query message, receive from at least one of the laboratory instruments, the patient sample result data, and transmit the patient sample result data to the client device.

In yet another example embodiment, a laboratory instrument of an integrated console environment includes a laboratory analyzer configured to generate patient sample result data by performing an analysis on a biological sample from a patient, and quality control data by performing an analysis on a control biological sample with known properties. The laboratory instrument also includes a first laboratory instrument memory configured to locally store the patient sample result data among a plurality of other patient sample result data and a first data access component at a first address configured to provide access to the first laboratory instrument memory. The laboratory instrument further includes a second laboratory instrument memory configured to locally store the quality control data among a plurality of other quality control data and a second data access component at a second address configured to provide access to the second laboratory instrument memory.

Additional features and advantages of the disclosed system, method, and apparatus are described in, and will be apparent from, the following Detailed Description and the Figures.

DETAILED DESCRIPTION

The present disclosure relates in general to a method, apparatus, and system for implementing an integrated console environment for diagnostic laboratory instruments. The example integrated console environment disclosed herein includes laboratory instruments and/or laboratory consoles that are configured to locally store laboratory data. These laboratory instruments and/or consoles include data access components ("DACs") that are configured to provide clients access to underlying data via one or more application programmable interfaces ("APIs"). The distribution of laboratory data at the laboratory instruments and/or consoles provides a relatively more reliable, scalable, and robust framework compared to more centralized systems. The distribution of the laboratory data at the laboratory instruments and/or consoles connected to the instruments also enables data analytic and persistent storage functionality to be distributed across an enterprise network based on the local location of the data.

As discussed above, known current centralized laboratory systems are subject to outages that can affect access to all of the centrally stored laboratory data. In contrast to these centralized systems, the example integrated console environment disclosed herein locally stores laboratory data on a laboratory console that is connected to a laboratory instrument that generates data. Client devices are able to access the laboratory console directly from the console to retrieve the stored laboratory data. Such a configuration enables client devices to access the stored laboratory data even with other parts of a network are offline or other laboratory instruments/consoles are offline.

The local storage of instrument data also reduces the traffic to any one data storage device. For instance, an enterprise may include twenty laboratory instruments. Client devices access only the laboratory instrument and/or respective console to which requested laboratory data is stored. This means that traffic from all the enterprise client devices will be distributed among the laboratory instruments instead of traffic being routed to a centralized database. This also means that traffic may be more distributed, resulting in fewer instances of limited bandwidth.

The distribution of the laboratory data to the laboratory instruments and/or consoles also enables associated functionality to be distributed. In contrast, a centralized data management system generally includes one or more servers that are configured with all applications needed to process and/or analyze the data. The example integrated console environment disclosed herein distributes applications and other functionality to the laboratory instruments and/or associated consoles such that only relevant or otherwise appropriate applications and other functionality are provided to a laboratory instrument/console. This distributed configuration enables applications and other functionality to be specifically tailored to the laboratory instrument/console. Further, changes to applications or updates to laboratory instruments only affect that instrument rather than the system as a whole.

Reference is made throughout this disclosure to laboratory data. As described in more detail below, laboratory data is data that is generated by a laboratory instrument. Laboratory data may include sample data that includes results or in-test data generated by performing one or more chemical or biological tests on a sample. Laboratory data may also include quality control ("QC") data that includes results or in-test data generated by performing one or more chemical or biological tests on a control sample with known properties. QC data is generally used to verify the accuracy or performance of a laboratory instrument and/or specific test. Laboratory data may also include configuration data of a laboratory instrument and diagnostic data associated with maintenance or operational performance of a laboratory instrument. The laboratory data may further include audit information associated with laboratory test verifications and/or operator verification.

Reference is also made herein to laboratory instruments and laboratory consoles. Laboratory instruments generally include one or more analyzers configured to determine one or more properties of a chemical or biological sample. Laboratory consoles include a computer, server, processor, etc. (comprising or communicatively coupled to a memory storing instructions for operation) that is configured to process, store, or otherwise manage data generated by a laboratory instrument. In some instances, a single enclosure may include one or more laboratory instruments and a laboratory console (e.g., an onboard workstation). In other instances, the laboratory console may be physically separate but communicatively coupled to one or more laboratory instruments in the same or separate enclosures. In certain instances herein, explicit reference to laboratory instruments includes implicit reference to the laboratory console communicatively coupled to the laboratory instrument.

Figure 1:
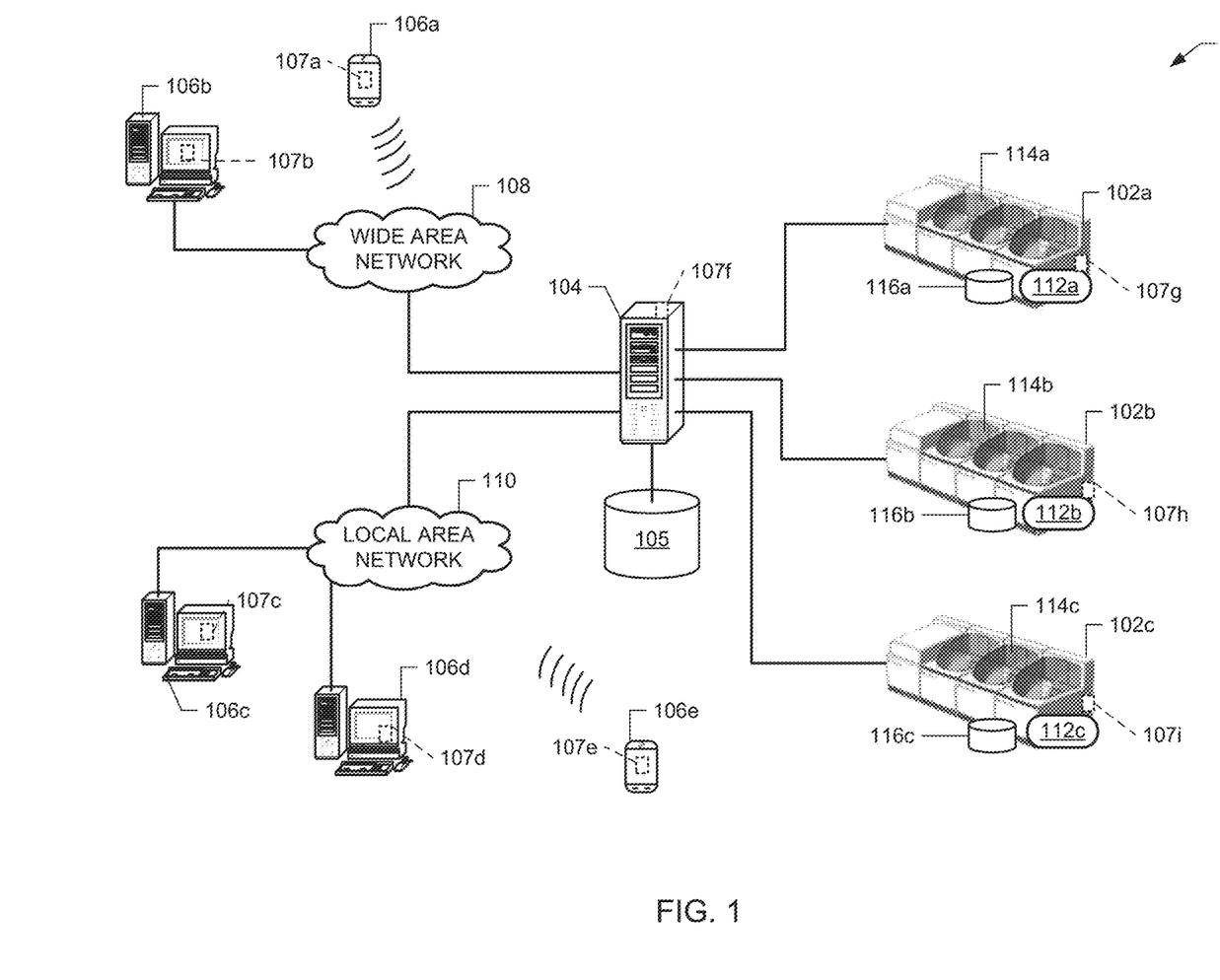
FIG. 1 shows an integrated console environment that includes distributed laboratory instruments communicatively coupled together via an application server, according to an example embodiment of the present disclosure.

FIG. 1 shows an integrated console environment 100 that includes distributed laboratory instruments 102a, 102b, and 102c communicatively coupled together via an application server 104. The example laboratory instruments 102 are configured to receive one or more chemical or biological samples, perform one or more chemical or biological tests on the samples, and record the progress/results of the tests.

While FIG. 1 shows the three laboratory instruments 102a, 102b, and 102c, it should be appreciated that other embodiments may include additional or fewer laboratory instruments.

The example application server 104 is configured to provide access to the laboratory instruments 102. The application server 104 is communicatively coupled to a centralized database 105, which may store relatively old or archived laboratory data. In some instances, the application server 104 includes a gateway, route, switch, etc. that enables client devices 106 to communicatively couple to the appropriate laboratory instrument 102 (or console of the laboratory instrument). For example, the client device 106a may transmit a request message for data that includes a network address of the laboratory instrument 102a (or a network address of a DAC on the laboratory instrument 102a). The application server 104 uses the specified network address to route the request message to the specified laboratory instrument 102a.

In other instances, the application server 104 may include an interface that isolates the laboratory instruments 102 from direct access of the client devices 106. For example, the client devices 106 may transmit request messages that include a network address of the laboratory instruments 102. Responsive to receiving the request messages, the application server 104 transmits a separate request message to the specified laboratory instrument 102, receives the requested data, and creates a response message for the client devices 106 including the requested data.

The client devices 106 may connect to the laboratory instruments 102 via any wide area network 108 (e.g., the Internet) and/or local area network ("LAN") 110. For example, as shown in FIG. 1, the application server 104 is communicatively coupled to client devices 106a and 106b via a wide area network 108 (e.g., the Internet) and communicatively coupled to client devices 106c, 106d, and 106e via a local area network ("LAN") 110. In some instances, the client devices 106 may use a virtual LAN ("VLAN") or other secure tunnel to directly connect to the laboratory instruments 102 via network 108 or 110.

The example client devices 106, the application server 104, and/or the laboratory instruments 102 may include one or more clients 107 configured to access, modify, analyze, etc. laboratory data stored at databases 116. As discussed in more detail below, the clients 107 are configured to access a DAC associated with the desired data. Each DAC is configured with the data hierarchy or structure of the stored laboratory data and provides an interface for the clients that masks or otherwise hides the structure of the underlying data. This configuration enables the clients 107 to access disparate laboratory data stored in different laboratory instruments 102 without having to be programmed with knowledge of the underlying storage structure (e.g., file structure) of the laboratory data or the format of the laboratory data. The client-server architecture of the DAC is discussed in further detail in conjunction with FIG. 3.

The example laboratory instruments 102 of FIG. 1 also include an instrument console 112 (e.g., a laboratory console) configured to manage data storage, data access, and data management. The laboratory instruments 102 further include one or more analyzers 114 configured to analyze a chemical or biological sample and generate corresponding laboratory data from the analysis. The example instrument console 112 receives and stores the generated data from the analyzers 114 to local database 116. The example database 116 may include, for example, a SQL Server database.

Figure 2:
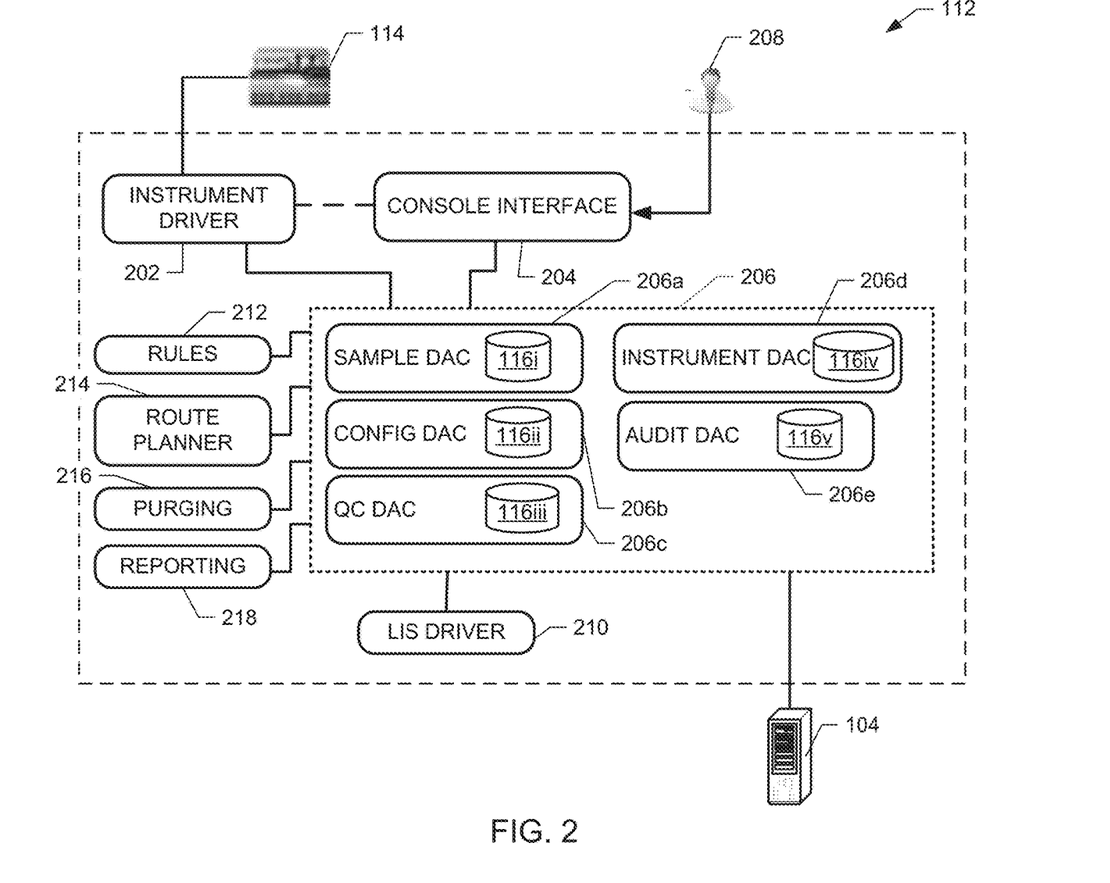
FIG. 2 shows a diagram of an instrument console of the laboratory instrument of FIG. 1, according to an example embodiment of the present disclosure.

FIG. 2 shows a diagram of the example instrument console 112 of FIG. 1. The instrument console 112 may be implemented on a computer, laptop, tablet computer, server, processor, etc. located on the laboratory instrument 102 or communicatively coupled to the laboratory instrument 102. The example instrument console 112 is communicatively coupled to the laboratory analyzer 114 via an instrument driver 202. The example instrument driver 202 is configured to control and query the analyzer 114 based, for example, on commands provided by an operator via a console interface 204, commands received from remote client devices 106, and/or commands received via the application server 104. The commands may include, for example, an instruction to perform one or more tests on a biological sample. The example instrument driver 202 is also configured to transmit data generated by the laboratory analyzer 114 to a DAC 206 (e.g., the DACs 206a to 206e) for storage in the database 116. The instrument driver 202 may operate as, for example, a Windows service and/or an Internet Information Service ("IIS") plugin that provides an external API as a Representational State Transfer ("REST") web service endpoint.

The example console interface 204 includes one or more clients and/or applications that are configured to enable an operator 208 to control the laboratory analyzer 114, view generated laboratory data, analyze laboratory data, and/or edit/delete laboratory data. The example console interface 204 is communicatively coupled to the DAC 206 to enable the clients and/or applications to access laboratory data stored to the database 116. The console interface 204 may also provide diagnostic, instrument, audit, or QC functionality for the operator.

The example DAC 206 of FIG. 2 includes a dynamic-link library ("DLL") that encapsulates laboratory data and business logic. As discussed in more detail below, the DAC 206 comprises one or more APIs that enable clients and/or applications (e.g., the console interface 204) to access underlying laboratory data without the clients or applications having to know the framework in which the laboratory data is stored. The DAC 206 of the illustrated example includes five application-specific DACs that are each connected or otherwise communicatively coupled to underlying portions of the database 116. For example, the sample DAC 206a is configured to provide access to sample data stored at the database 116i, the configuration DAC 206b is configured to provide access to configuration data of the laboratory analyzer 114 and/or the instrument console 112 stored at the database 116ii, and the QC DAC 206c is configured to provide access to QC data stored at the database 116iii. Additionally, the instrument DAC 206d is configured to provide access to instrument data stored at the database 116iv and the audit DAC 206e is configured to provide access to audit data stored at the database 116v. While FIG. 2 shows the databases 116i to 116v as being part of the database 116, in other embodiments each of the databases 116i to 116v may be a separate database. For example, the database 116i may be included on a solid state drive ("SSD") while the database 116ii is included on a serial ATA ("SATA") drive. Further, while FIG. 2 shows the five DACs, it should be appreciated that the instrument console 112 may include additional or fewer DACs. For instance, a DAC may be provided for each type of analyzer 114 included within the laboratory instrument 102 and/or a DAC may be provided for each type of test that may be performed by the analyzer 114.

In some embodiments, each of the DACs may be assigned one or more network addresses. For instance, a client device 106 (or operator 208) may use a network address (e.g., an IP address) within a request message transmitted to the DAC 206 to directly pull and access data at the database 116. The application server 104 or other switch uses the DAC network address within, for example, a header of the request message to route the request message to the appropriate laboratory instrument 102, instrument console 112, and/or DAC 206. One advantage of such a configuration is that the individually addressable DACs 206 enable the laboratory instrument 102 and/or the instrument console 112 to be web-based. That is, both the laboratory instruments 102 and the DAC 206 are remotely accessible via an interface by providing the DAC's IP address on a web browser (or other interface) at the client device 106. In some embodiments, the client devices 106 and/or the clients 107 may use web services to communicate with the DACs 206.

In some embodiments, the laboratory instrument 102 and/or the application server 102 is located behind a firewall such that a static IP address is provided to each of the DACs 206 and/or the instrument console 112. Alternatively, a different or dynamic public IP address is provided to the DACs 206 and/or the laboratory console 112 each time the instrument 102 is connected to the Internet or Intranet. In other embodiments, the instrument 102 (or the underlying DACs 206 and/or the console 112) is provided with a static IP address and is not located behind a firewall. Static IP addresses may make it easier for users of other instruments or a central computer within the same laboratory to access the instrument 102 and data provided by the DACs 206. In yet other embodiments, the laboratory instrument 102 (or the underlying DACs 206 and/or the console 112) is also connected to the Internet without being protected by a firewall, but is provided with one or more dynamic IP addresses.

In some embodiments, data from the DAC 206 is only available in a read-only format. In other embodiments, the data made accessible by the DAC 206 can be changed and modified, such as specific user configurations or software updates in the configuration DAC 206b. It should be appreciated that different permissions may be provided to the different DACs 206 so that only defined groups of operators and/or users may read or modify the underlying data for any given DAC.

The example instrument console 112 of FIG. 2 also includes a lab information system ("LIS") driver 210 configured to monitor messages related to test orders transmitted to the instrument console 112. The example LIS driver 210 transmits requests for new orders to, for example, the instrument driver 202 and/or the appropriate DAC 206. The LIS driver 210 also reports a status of the order including a notification of a completion of an order. The LIS driver 210 may determine changes to an order by monitoring changes to the underlying data associated with the order stored in the database 116. For instance, the LIS driver 210 may communicate with the sample DAC 206 to access sample data stored at the database 116i to determine a status of a corresponding order. The status of an order may be transmitted periodically to a client device 106 that requested the order and/or to a status webpage hosted by, for example, the application server 104. The status webpage may gather console information from the multiple laboratory instruments 102 to enable a site administrator to monitor the status of orders or tests within an entire lab or enterprise.

The example instrument console 112 also includes a rules component 212, a route planning component 214, a purging component 216, and a reporting component 218 to provide enhanced functionality for the laboratory data stored at the database 116. For instance, the rules component 212 implements business rules and data architecture rules to ensure laboratory data is stored according to predetermined formats. The rules component 212 may also specify when laboratory data is moved between different types of databases. For instance, a rule may specify that relatively new laboratory data is to be stored to temporary storage (which is quickly accessible) while relatively old laboratory data is to be stored to a higher capacity persistent storage (e.g., the central database 105 of FIG. 1). The rules may also specify when laboratory data is to be offloaded from the laboratory instrument 102 to another database, such as the central database 105.

The example route planning component 214, the purging component 216, and the reporting component 218 are configured to manage the underlying laboratory data stored in the database 116 based on rules within the rules component 212. For instance, the route planning component 214 may manage to which of the DACs 206 laboratory data is to be stored and/or to which address at the central database 105 (or application server 104, client device 106, etc.) data is to be transmitted. As mentioned, the laboratory data may be migrated based on age. After (or during) a migration, the components 214, 216, and 218 may update the appropriate DACs 206 regarding whether specific laboratory data is no longer available to the DAC 206 or is now available to the DAC. The reporting component 218, may for instance, update data structures or files associated with the DACs 206 and/or data structures or files at the application server 104 that indicate where laboratory data is stored. The reporting component 218 may also update clients of changes to laboratory data in response to queries while the purging component 216 removes or deletes laboratory data that reaches a certain age.

Figure 3:
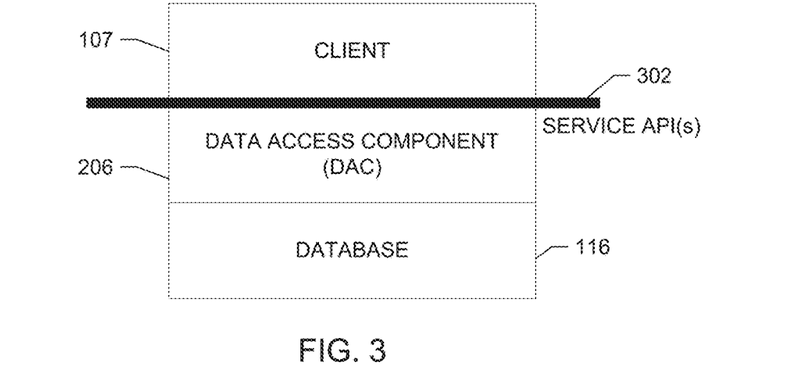
FIG. 3 shows an architecture diagram of a data access component in relation to a client and a database within the distributed client-server architecture of the integrated console environment of FIG. 1, according to an example embodiment of the present disclosure.

FIG. 3 shows an architecture diagram of the DAC 206 in relation to a client 107 and the database 116 within the distributed client-server architecture of the integrated console environment 100 of FIG. 1. The example client 107 may operate on any of the client devices 106, the application server 104, and/or the instrument console 112 of FIG. 1 that has access to any of the specific DACs 206. As shown in FIG. 2, the example DAC 206 and/or the database 116 is generally located on the laboratory instrument 102 at the instrument console 112.

Each DAC 206 straddles the client-server divide. The client and server code may be executing on different systems, and the communication protocol is via HTTP, so laboratory data must be converted by the DAC 206 appropriately on either side. The DAC 206 is implemented on a server or processor (e.g., the instrument console 112) of the laboratory instrument 102. The DAC 206 may be built on top of the ASP.Net Web API. The Web API is configured to listen for, receive, and dispatch server calls, parse arguments out of the URL, and process HTTP headers. Each DAC 206 may have to control its processes and configuration in IIS. Each DAC 206 accordingly may be packaged and deployed as a separate top-level IIS endpoint.

Any DAC 206 may be called from a client by creating and issuing an HTTP/REST request to the appropriate DAC endpoint. The server-side DAC 206 may include a project that exposes a one-for-one client-side API 302 for the DAC 206. Each call in the DAC 206 has a corresponding call in the client 107. In instances where the DAC 206 is called from a webpage, the REST request may be created and processed in JavaScript rather than C #.

The example DAC 206 provides access to create, read, and/or modify laboratory data The example DAC 206 may also be configured to perform aggregate queries of the contents of the associated database 116. The example DAC 206 provides enhanced create, read, update, and delete ("CRUD")—and query interface for the client 206 while hiding the details of the underlying database 116. The DAC 206 may be implemented, for example, as an IIS-hosted REST web service. This configuration enables the client 107 to access the DAC 206 in a variety of ways by relying on open standards. As long as the client 107 can access a network address of the DAC 206 and has a name of a service endpoint, the client 107 can connect to the requested laboratory data at the database 116 via the DAC 206.

It should be appreciated that multiple instances of the same DAC 206 may be implemented in different laboratory instruments 102 across the integrated console environment 100. For instance, each instrument console 112 may include an instance of a DAC for sample information. Any individual client (including other DACs) can connect to one, two, or all available instances of the sample DAC in the lab. In this instance, the client 107 has to have permission or access to each of the laboratory instruments 102 in addition to having the network address of each instance of the DAC on the laboratory instruments 102.

The example DAC 206 includes or provides a website service via an API 302. In some instances, the DAC 206 may provide the API 302 using IIS. The illustrated DAC 206 embodies an endpoint that enables the clients 107 to connect to the DAC. The API 302 provides access to services implemented, for example, as REST/JavaScript Object Notation ("JSON") endpoints to be accessible by, for example, Windows Presentation Foundation ("WPF") applications and webpage clients 107. The DAC 206 may also use the REST protocol for messaging. This configuration enables each API 302 to take in a small number of arguments (of built-in types) and an optional JSON object, and return a single JSON object or built-in type. In many cases the JSON data may be the serialized result of an object tree, or of a list query. In some cases the JSON data may be a return error status code with accompanying messages. This configuration also enables the DACs 206 to structure and define the API 302 as appropriate for both the underlying laboratory data and the usage/access patterns as required by the clients 107.

The architecture shown in FIG. 3 includes a library with convenience functions and utilities to assist in implementing DAC client-side APIs 302. These include functions to create and manipulate heterogeneous maps/dictionaries of laboratory data that can be read from or written to JSON, common error handling hooks, security, and methods for connecting to the DAC 206 server-side from the client 107. Each DAC 206 may contain a variety of function calls of varying styles. For instance, the DACs 206 may retrieve an object (e.g., retrieve laboratory data), comment a new or edited object (e.g., store laboratory data), return list queries (e.g., return a list of summarized laboratory data based on search criteria provided by the client 107), or perform an action request (e.g., request a component, application, or service to perform an action on the laboratory data).

Object retrieval calls by the client 107 to the DAC 206 acquire a small set of information (i.e., one or more names or unique identifier numbers) that is used to uniquely identify a chunk of laboratory data. The return value provided by the DAC 206 to the client 107 is a JSON data structure, list or file that can be de-serialized into a run-time C # object tree. Additionally, access to the DACs 206 may require an instanced object rather than using static functions, depending on how the DAC is configured. It should be appreciated that a single DAC function could return multiple high-level objects to the client 107 using JSON. The client-side API implementation pulls the objects out of the JSON wrapping to conveniently transmit the object-based laboratory data to the clients 107.

Object commit calls by the client 107 to the DAC 206 are used to accept as a message body one or more object graphs in JSON. The arguments may include validation criteria such as timestamps. However, information needed for the DAC 206 to correctly perform the commit will probably already be contained within the object(s) being committed.

List queries transmitted by the client 107 to the DAC 206 are used to summarize or monitor sets of laboratory data. The list queries take in arguments that scope the query (by time, status, or other conditions) and return the equivalent of a .Net DataSet, but transported with the JSON/heterogeneous-collection tools. The set of criteria available for constraining the query is based on the configuration of the DAC 206. The list queries are implemented on the server-side at the DAC 206 with stored procedures or generated SQL code. The structure of the corresponding API call will generally match the implementation. When dealing with large result sets, the API 302 of the DAC 206 may be configured to implement one or more strategies. For instance, the API call might specify that only the first N items will be returned, possibly based on sorting order (such as a timestamp). Alternately, the API 302 might be built with a paging mechanism, where the client 107 specifies that it wants the M'th through N'th items in the list. Finally, the API 302 may stream the full result set and leave it up to the client 107 to handle paging or other presentation logistics.

Action requests transmitted by the client 107 to the DAC 206 are used as simple procedure calls. Exceptions or status codes can be used to handle failures. Some action requests may require ongoing monitoring by the client 107 that made the original request. In these instances, the DAC 206 may return a unique memento (often a GUID) that can be used by the clients 107 on subsequent updates.

The example client 107 of FIG. 3 is configured to implement a main body of functionality in a device such as the client device 106, the application server 104 and/or the instrument console 112. The example client 107 may include, for example, an application that is configured to interact with a user. The application may include a stand-alone application (e.g., an app) and/or a webpage. The example client 107 may also include a windows service that includes one or more executables configured to operate continuously in a background of a device. A windows service includes, for example, a service that monitors incoming messages for certain laboratory data or instrument status. The example client 107 may also include a web service that enables the client 107 to function as a client of another DAC.

An individual client 107 is configured to have a well-defined scope of responsibilities and will generally operate independent of clients on the same or other devices. Laboratory data may be shared between different clients on the same or other devices. However, the shared data is retried and edited through a common DAC (e.g., the DAC 206). The shared laboratory data is generally not communicated between the clients.

The example database 116 of FIG. 3 may include, for example, a database, a directory tree of files on a disk, or some combination of the two. Generally, database schemas may use primitive data types. In some instances, the database may use or store encoded information. The files on a disk may include primitive data types used outside of aggregating structures. The files on the disk may be, for example, JSON, Extensible Markup Language ("XML"), etc. Large auxiliary data such as images or complex calibration curve data may be stored to the database 116 in an appropriate format. Alternatively, large auxiliary data may be pointed to by a database text field or JSON property specifying the path where the data can be found.

The example database 116 is configured to maintain persistent and/or transient laboratory data in a secure format that can be backed up for safety and auditing purposes. The database 116 may include one or more rules specifying units or types of laboratory data to reduce the complexity of the API 302. For example, a rule may specify that scalar laboratory data values are to be stored in either canonical units or paired with an enum indicating which units are used. Another rule may specify that dates and times are stored in Coordinated Universal Time ("UTC"). Yet another rule may specify that timespans are to be stored in seconds using floating-point values for sub-second resolution. Other rules may specify that liquid volume is to be stored as milliliters and temperature is to be stored using Celsius values.

As shown in FIG. 3, the example database 116 is accessible via only the DAC 206. Such a configuration provides an efficient one-to-one relationship between the DAC 206 and the database 116 such that the DAC 206 only provides access to the proximately located database 116. However, in other examples, the database 116 may be accessible by other DACs and/or the example DAC 206 may access other databases.

Data Management Using DACs

The data management policies of the architecture of the integrated console environment 100 rely on having each piece of data owned by one component (e.g., the DAC 206) of the architecture. With hierarchical data such as object graphs, the owner of all items must be the same as the owner of the topmost item. This yields decoupled graphs of objects whose ownership can clearly be tracked in the system 100 and trusted. The example DAC 206 of FIGS. 2 and 3 is the source of truth for a set of logically coherent data items of laboratory data. The DAC 206 may cache sample results in Radom Access Memory ("RAM") for performance and store persistent laboratory data on a disk within the database 116. To external parties (such as the client devices 106), the DAC 206 itself is the source of truth.

The laboratory data stored in the databases 116 has to be specifically accessed or pulled. For instance, the client 107 uses an API call to the appropriate DAC 206 to request laboratory data. All data returned by the DAC 206 is timestamped, or, in the case of list queries, is implicitly transient and read-only. When laboratory data is modified by the client 107, the client 107 makes a separate call to the DAC 206 to commit the change. The example DACs 206 ensure that no commit is accepted unless its fetch timestamp is greater than the timestamp of the current version of the data. This means that a commit might fail, in which case the DAC 206 transmits an exception. The client 107 may then decide how to deal with the failure. For critical object graphs that are likely to have commit collisions (such as a sample graph), the DAC 206 may provide tools to facilitate the error handling. These tools may include a merge capability between two graphs which would only fail if conflicting data changes were found. Another tool may include an audit/playback editing mechanism so that edits applied to older (committed) graphs are automatically applied to newer graphs. These tools may further include a generic locking function (provided as a database utility component) such that a lock must be obtained before an edit/commit can be made, and is thus guaranteed to be safe.

Data within the laboratory instruments 102 may be monitored by the LIS driver 210 performing repeated queries, usually on a timer. This may be useful for list query operations that are used to display, for instance, a set of samples that need attention, or a set of system alerts. Monitoring of changes to individual objects can also be done by examining an object graph's timestamp.

In some instances, the DACs 206 may be configured to push or transmit data without a prompt. In these instances, the LIS driver 210 may at specified intervals instruct the DAC 206 to transmit laboratory data to a specified endpoint, such as the client device 106, the client 107, and/or another laboratory instrument 102. Such a configuration may be used to periodically migrate laboratory data between different databases 116 and/or migrate laboratory data to the centralized database 105.

The example database 116 may include an engine that uses an SQL Server. Further, each of the DACs and each DAC that accesses a particular database 116 are configured to use its own catalog. Tables may contain only built-in data types provided by a SQL Server. XML embedded in columns, while valid in a SQL Server, may be used in conjunction with a) breaking laboratory data out into specific columns and/or b) putting laboratory data in a JSON file on a disk. Tables may contain key references to tables in other catalogs, but such external foreign keys may be used judiciously to avoid excessive coupling between catalogs. The example architecture provides a micro-Object-Relational Correlator ("ORC") that can be used by the clients 107 to define classes that roughly correspond to tables, and to easily write and read simple, record-level data. ORC is a tool used from within the DAC 206 to conveniently interface with the engine of the database 116 using standard object-orientated and reflection techniques. It should be noted that ORC does not attempt to be an invisible persistence layer as do many ORMs. ORC is a record- or row-level tool. It may not operate on object trees or sub-trees, but only on individual objects. This provides the DACs 206 with a great deal of flexibility in balancing the costs/performance of retrieves and commits, at the slightly elevated cost of having to manage trees of objects themselves. Such a configuration encourages simplicity in both the schemas and the design of the APIs 302 of the DACs 206. ORC may be implemented as an interface definition fulfilled by correlating object classes, as well as an engine class that implements the actual database access methods.

In some instances, a foreign key stored in a table may refer to another table either in the same catalog or in another catalog on the same instance of SQL Server. In some cases, it may be necessary to maintain key information that refers to an entirely different DAC. For instance, a middleware-type application or client 107f on the application server 104 of FIG. 1 may track sample information from multiple instruments. The client 107f may track sample IDs where the samples are owned by the laboratory instruments 102a and 102b. In fact, in this situation the sample IDs from the multiple instruments 102 may not be guaranteed to be unique across the middleware. The client 107f accordingly uses a combined key of the sample ID and the name or address of the "owning" instrument 102 to fully disambiguate the sample laboratory data.

The example client-server architecture of the environment 100 provides a serialization scheme that enables individual objects or whole hierarchical trees of objects to be streamed to a file (or over any other stream-based data sink) within the database 116. The scheme uses simple name/value pairs of built-in data types, formatted in JSON for web compatibility and ease of parsing. Data stored in this form is typically expected to be used as a block by the clients 107. In other words, when any piece (or sub-tree) of laboratory data is needed, it is probable that the client 107 may use other portions of the source data. For instance, a client or application that is configured to configure a laboratory instrument generally uses all of the configuration laboratory data at the same time. Accordingly, the configuration laboratory data is stored as one or more blocks to be commonly accessed by the client 107 via the DAC 206 from the database 116.

It should be appreciated that file stores will often co-exist with an associated database store that will contain key information used to a) look up specific instances of the data or b) report on all available instances, either as a list or in aggregate. In this case, a master copy of the data is located at the file store and the database information is essentially a performance optimization copy of the key data. Several useful properties fall out of this scheme including the fact that the database 116 may always be reconstructed from the full set of master files on disk. Additionally, a maximum capacity of the database 116 is limited by disk space and read/write times rather than by database performance. Further, data backups can be done without any database impact. Moreover, for clients 107 operating on the application server 104, the reliability and capacity of the underlying media may be adjusted as needed by local hospital/lab IT and managed using standard tools.

Figure 4:
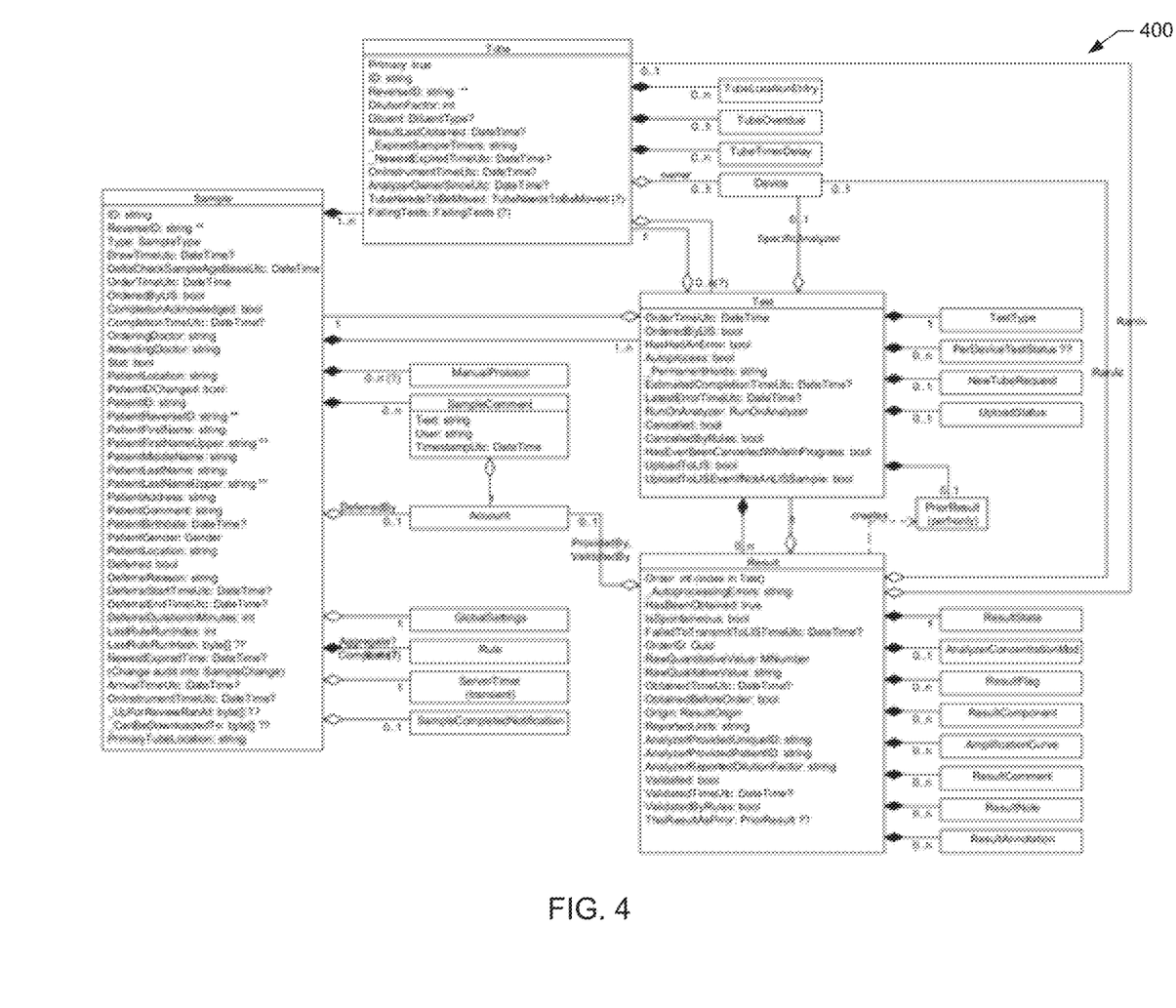
FIG. 4 shows a diagram of a data structure illustrating how sample laboratory data may be modeled and stored to a database, according to an example embodiment of the present disclosure.

FIG. 4 shows a diagram of a data structure 400 showing how sample laboratory data may be modeled and stored to the database 116*i* using a file-based and object framework. Generally, sample laboratory data is inherently hierarchical, with objects within a data tree relating to one another. For example, test laboratory data is related to result laboratory data for a biological sample. The analyzer 114 that is working with a specific sample will oftentimes be working with major sub-trees in the hierarchy, whether by creating a new sample instances, reporting result status to the LIS driver 210, or adding new results.

The database 116*i* may also include laboratory data for hundreds of thousands, if not millions of samples. Querying for specific samples within the database 116 by traversing and opening files would be overly burdensome. Therefore, the core data model shown within the data structure 400 is augmented on disk of the database 116 with high-performance database tables that are used for fast querying. However, only certain of the laboratory data shown within the data structure 400 are represented in a fast-query table. For instance, the LastRuleRunIndex value, the PatientMiddleName value, the PatientAddress value, the DeferralReason value, and the DeferralStartTime are typically not included within a query search and are accordingly left out of the fast-query table. Therefore, the data representation of the fast-query tables can be significantly smaller, thereby decreasing the processing burden on the engine of the database 116.

It should be appreciated that the data structure 400 of FIG. 4 shows just one possible way to structure laboratory data. In other embodiments, the laboratory data may be partitioned into multiple segregated files (e.g., base data, tests & results, audit information, etc.). In these embodiments, a separate DAC 206 may be used for each class or type of segregated file.

Example Laboratory Data Embodiments

Figure 5:
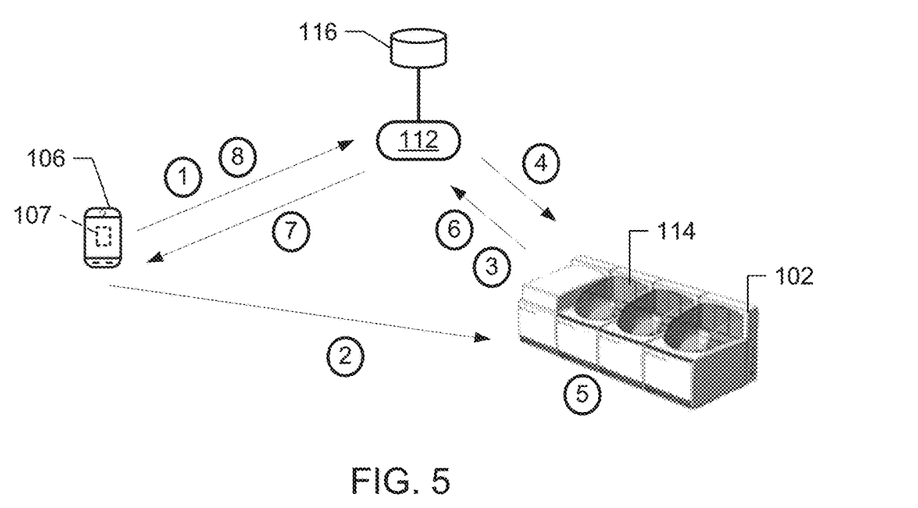
FIGS. 5 to 7 provide examples of how laboratory data at one or more laboratory instruments may be made available to client devices via a data access component on an instrument console, according to an example embodiment of the present disclosure.
Figure 6:
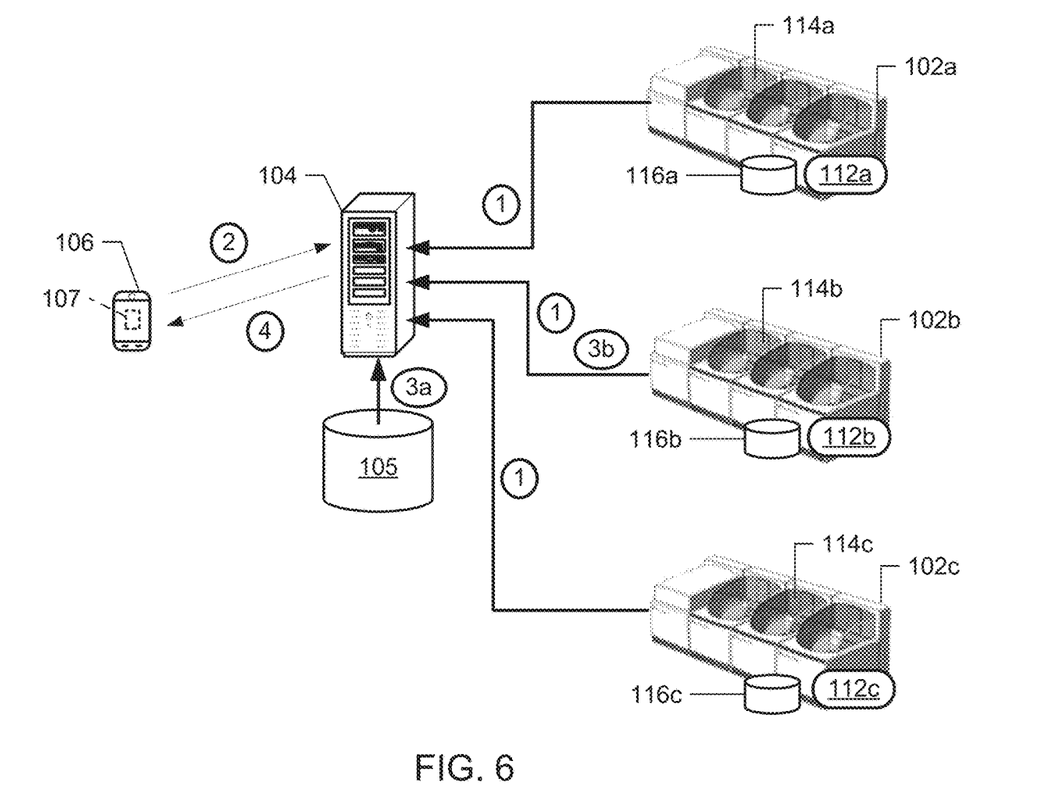
Figure 7:
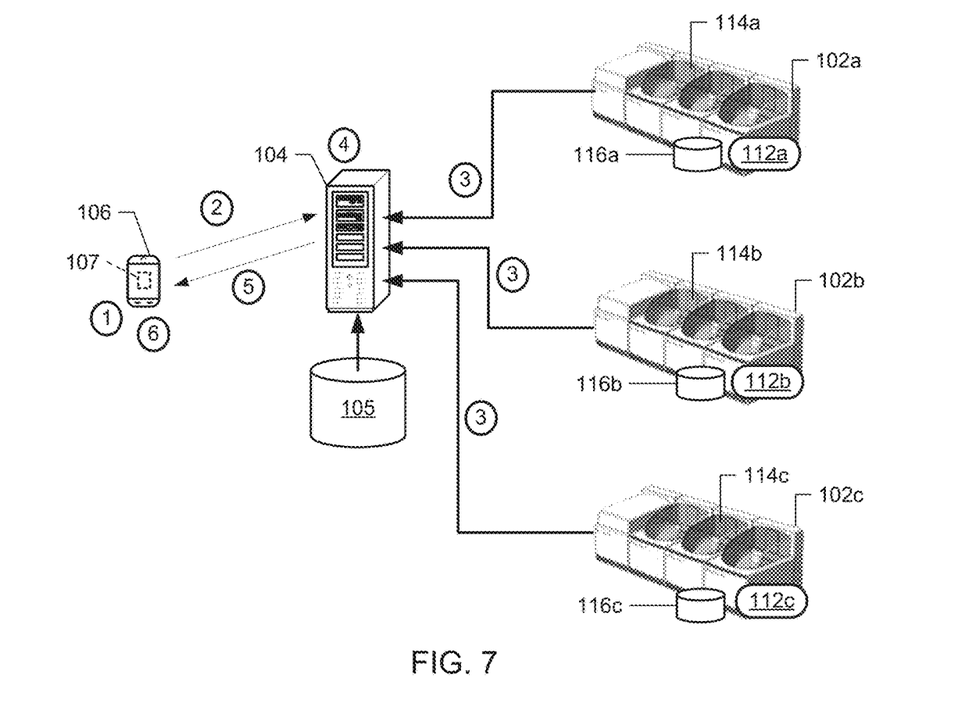

FIGS. 5 to 7 provide examples of how laboratory data at the laboratory instrument 102 may be made available to the client device 106 via a DAC on the instrument console 112. FIG. 5 shows a diagram where a user of the client device 106 orders a test on the laboratory instrument 102. In this example, the instrument console 112 is separated logically (and/or physically) from the laboratory instrument 102. In other embodiments, the instrument console 112 may be replaced by or operate in conjunction with the application server 104.

In the illustrated example, the client device 106 uses the client 107 to send the instrument console 112 an order to conduct a test (step 1). A user of the client device 106 also provides a sample associated with the order to the laboratory instrument 102 (step 2). The laboratory instrument 102 then informs the instrument console 112 that the sample has arrived (step 3). The instrument console 112 updates a status to indicate the sample is present in the laboratory instrument 102. The instrument console 112 also sends the parameters of the order to program the analyzer 114 at the laboratory instrument 102 to perform the desired test (step 4). The analyzer 114 then runs or performs the test on the sample (step 5).

During and/or after the test, the laboratory instrument 102 reports the results of the test to the instrument console 112 (step 6). The instrument console 112 stores the test results to the appropriate database 116 within the file structure framework discussed above. The example instrument console 112 also sends a notification to the client device 106 that the test results are available (step 7). The user of the client device 106 may then use the client 107 to access and view the results of the test (e.g., the laboratory data) stored in the database 116 (step 8).

FIG. 6 shows an example where the application server 104 is configured to periodically aggregate/consolidate laboratory data in the centralized database 105 for long term warehousing and analytics. The laboratory instruments 102 may be configured to store the laboratory data for a specified time period (e.g., 30, 60, or 90 days) before the data is migrated to the centralized database 105. After this specified time, the application server 104 pulls the laboratory data from the laboratory instruments 102 (step 1).

In this example, a user of the client device 106 uses the client 107 to transmit a request message for specific laboratory data (e.g., a request for pediatric specimens for the last six months that were flagged as having an abnormally high property) (step 2). A DAC at the application server 104 searches the warehoused data at the centralized database 105 and accesses laboratory data that matches the specified criteria (step 3a). The DAC at the application server 104 also searches the laboratory instruments 102 for laboratory data that matches the specified criteria (step 3b). In this manner, the DAC at the application server 104 operates as a client to request laboratory data from the DACs at the instrument consoles 112 of the laboratory instruments 102. In this illustrated example, only the laboratory instrument 102*b* has the requested data. After compiling the laboratory data from the different sources, the example application server 104 makes the laboratory data available to the client 107 on the client device 106 (step 4). The client 107 may then perform one or more analysis on the laboratory data based on inputs from the user.

FIG. 7 shows an example where the application server 104 is used to acquire diagnostic or instrument laboratory data from the laboratory instruments. In this example, a user of the client device 106 accesses or opens a client 107 configured to determine supplies needed for the laboratory instruments 102*a* to 102*c* (step 1). The client 107 transmits a query to the application server 104 requesting supplies that are in need by the laboratory instruments 102 (step 2). The application server 104 may use a DAC configured for accessing the laboratory instruments 102 to transmit or broadcast an asynchronous web services call to all of the laboratory instruments regarding needed supplies (step 3). In this manner, the DAC at the application server 104 operates as a client to request the supplies.

Each instrument DAC 206*d* at the respective instrument console 112*a* to 112*c* of the respective laboratory instruments 102*a* to 102*c* access, for example, the respective database 116*iv* to access instrument or diagnostic laboratory data. For instance, each of the analyzers 114*a* to 114*c* may include sensors that detect fluid or other supply chemical levels. A processor on the analyzer 114 may transmit to the respective database 116*iv* a message to store indications as to which fluids or other chemicals are below a predetermined threshold. The respective instrument DACs 206*d* read the contents of the respective databases 116*iv* to determine fluids or other chemicals that are in need by the respective analyzers 114*a* to 114*c*. The DACs 206*d* accordingly transmit a message to the application server 104 including identifications (and/or quantities) of the fluids or chemicals needed in addition to other needed supplies (step 3). The message may also identify the specific analyzer 114 that needs the fluids or chemicals.

The example application server 104 compiles the responses from each of the laboratory instruments 102 (step 4). In some instances, the application server 104 (or client 107) may determine total quantities of each supply needed in addition to each laboratory instrument that needs each supply. The application server 104 then makes available the supply laboratory data to the client 107, which renders and displays the data to the user (step 5). The user may then use the data to determine which supplies are needed and accordingly restock the laboratory instruments 102 (step 6).

In some instances, the instrument console 112 may operate in conjunction with the analyzer 114 to predict supply usage based, for example, on orders received. The instrument console 112 may then store to the database 116*iv* indications of which supplies are needed to fulfill the orders. In some instances, the instrument DAC 206*d* or other component of the instrument console 112 may generate a message for the application server 104 and/or the client devices 106 indicating which supplies are needed to be able to complete the ordered tests. Such a message may be an alert or alarm that is transmitted from the laboratory instrument 102 under conditions defined by, for example, the rules 212 of FIG. 2.

Laboratory Data Storage Embodiments

Figure 8:
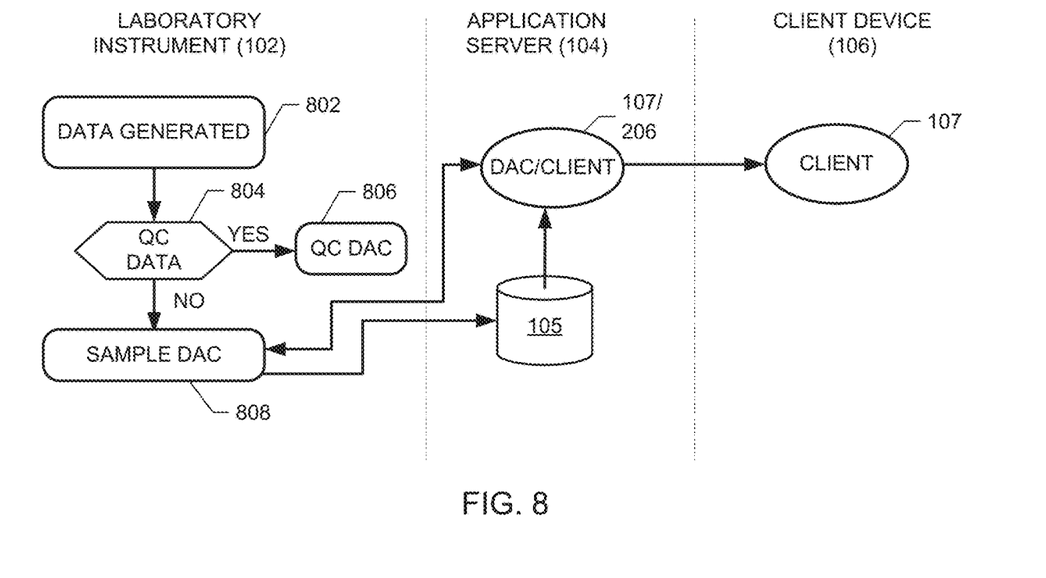
FIGS. 8 to 10 show diagrams of possible configurations of data storage, according to an example embodiment of the present disclosure.
Figure 9:
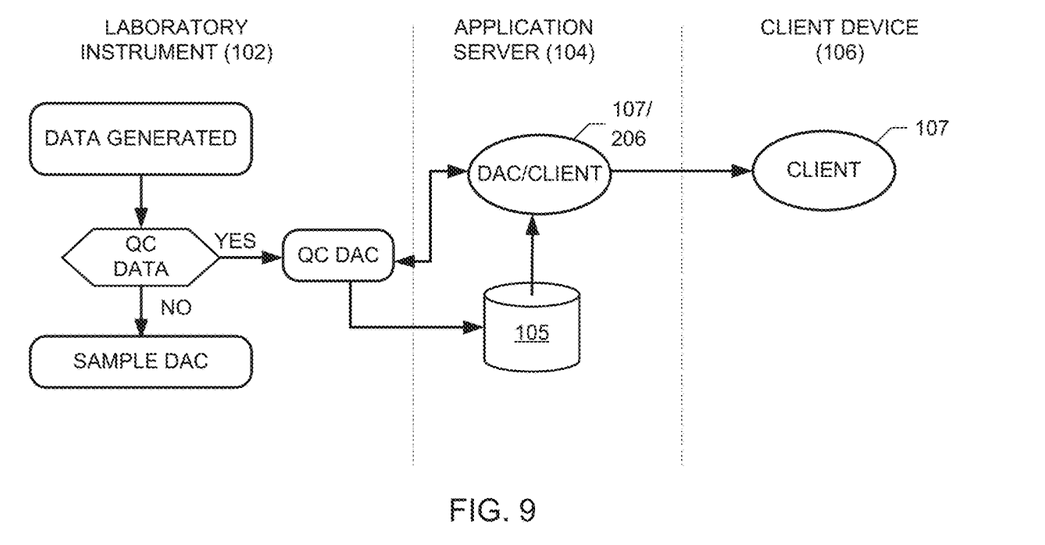
Figure 10:
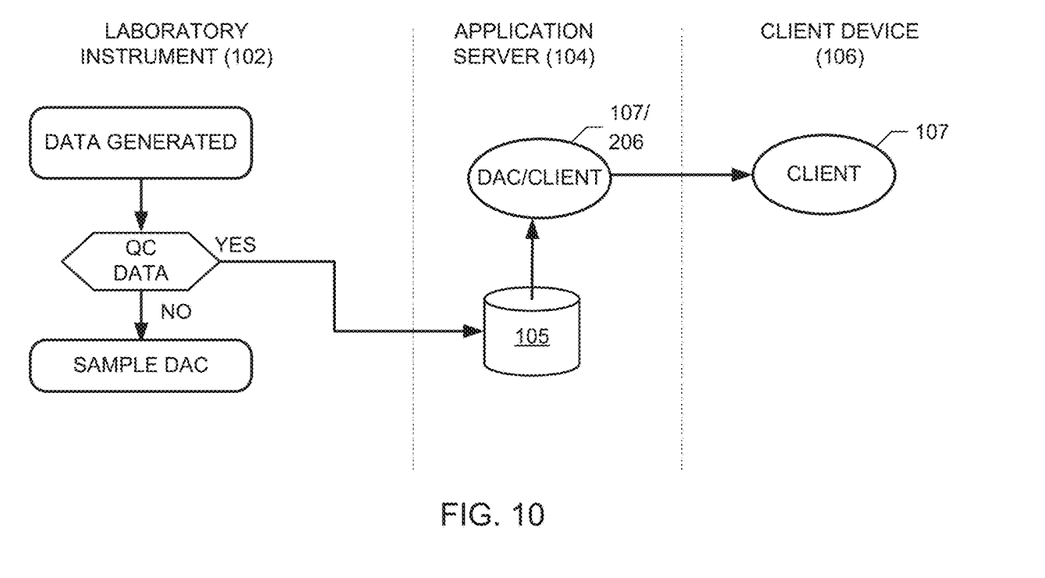

As discussed above, laboratory data may be stored on the database 116 at the respective laboratory instruments 102 and/or at the centralized database 105. The specific configuration as to where which types of laboratory data may be stored is dependent on the desires of each enterprise that uses the integrated console environment 100 of FIG. 1. FIGS. 8 to 10 show diagrams of possible configurations of data storage.

In particular, FIG. 8 shows an embodiment where QC laboratory data and sample laboratory data are stored at respective databases 116*i* and 116*iii* on the laboratory instrument 102. The example instrument console 112 determines if the data generated by the laboratory instrument 102 (block 802) is QC or sample data using, for example, an identifier associated with the test that generated the data (block 804). For example, tests run using known or control samples may be associated with a certain type of identifier included within an order code or identifier. The QC laboratory data is accordingly stored at the database 116*iii* accessible by the QC DAC 206*c* of FIG. 2 (block 806) and the sample laboratory data is stored at the database 116*i* accessible by the sample DAC 206*a* (block 808). In this embodiment, the sample DAC 206*a* may periodically push the sample data to the centralized database 105 after a time period (e.g., weekly, monthly, bimonthly, quarterly, yearly, etc.).

In the illustrated example of FIG. 8, the client 107 on the client device 106 transmits a sample data request to the application server 104. A DAC and/or client 107/206 on the application server 104 accesses the sample data from either the centralized database 105 and/or the sample database 116*i*. In an example, a DAC 206 on the application server 104 may attempt to locate the data at the centralized database 105 by performing a query of the laboratory data stored. The DAC 206 on the application server 104 also transmits a query message to the sample DAC 206*a* at the laboratory instrument 102. After receiving the requested sample laboratory data, the DAC/client 107/206 may perform an analysis on the data and make the raw or analyzed data available for view via the client 107 on the client device 106. It should be appreciated that the DAC/client 107/206 of the application server 104 accesses the QC DAC 206*c* (without accessing the centralized database 105) in instances where QC laboratory data is requested.

In contrast to FIG. 8, FIG. 9 shows a configuration where QC laboratory data is stored locally to the QC database 116*iii*, accessible by the QC DAC 206*c* on the laboratory instrument 102. The laboratory data at the QC DAC 206*c* is periodically transferred or copied to the centralized database 105. The sample laboratory data is stored only at the sample database 116*i*, accessible by the sample DAC 206*a*. In this embodiment, a request from the client 107 for QC data causes the DAC/client on the application server 104 to search the centralized database 105 and/or the database 116*iii* for the QC data. A request for sample laboratory data causes the DAC/client on the application server 104 to search only the database 116*i* via the DAC 206*a* for the sample data.

FIG. 10 shows an embodiment where sample laboratory data is stored to the sample database 116*i* accessible by the sample DAC 206*a* while QC laboratory data is transmitted directly to the centralized database 105. Here, the instrument console 112 of the laboratory instrument 102 does not include a QC DAC or a portion of the database 116 allocated for QC data. In this embodiment, a request from the client 107 for QC data causes the DAC/client 107/206 on the application server 104 to search only the centralized database 105. Similar to FIG. 9, a request for sample laboratory data causes the DAC/client on the application server 104 to search only the database 116*i* via the DAC 206*a* for the sample data.

It should be appreciated that the examples shown in FIGS. 8 to 10 are only illustrative of how laboratory data may be stored in the integrated console environment 100 of FIG. 1. In other examples, the application server 104 may only migrate laboratory data to the centralized sever 105 that corresponds to data generated among multiple laboratory instruments 102 from samples collected from the same speciesism or patient. Alternatively, the application server 104 may be configured to store only data structures of query results at the centralized data store. The query results may specify, for instance, which of the laboratory instruments 102 stores data associated with, for example, a particular patient, test, order, etc.

CONCLUSION

It will be appreciated that all of the disclosed methods and procedures described herein can be implemented using one or more computer programs or components. These components may be provided as a series of computer instructions on any computer-readable medium, including RAM, ROM, flash memory, magnetic or optical disks, optical memory, or other storage media. The instructions may be configured to be executed by a processor, which when executing the series of computer instructions performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A laboratory instrument apparatus comprising:
a laboratory analyzer configured to receive a biological sample from a patient and a control biological sample and configured to perform one or more tests comprising an analysis on the biological sample and an analysis on the control biological sample;
a laboratory processor of the laboratory instrument apparatus configured to receive from the laboratory analyzer both patient sample result data based on the analysis on the biological sample from the patient, and quality control data based on the analysis on the control biological sample, the quality control data being indicative of an accuracy or performance of the laboratory instrument apparatus or a specific test of the one or more tests performed by the laboratory analyzer; and
a local database configured to locally store the patient sample result data among a plurality of other patient sample result data, the local database being located on the laboratory instrument apparatus;
wherein the laboratory processor is configured to operate in conjunction with the laboratory analyzer to:
determine whether data generated by the laboratory analyzer comprises the patient sample result data or the quality control data,
conditioned on the generated data comprising the patient sample result data, store the patient sample result data on the local database,
conditioned on the generated data comprising the quality control data, transmit the quality control data to be stored in a centralized database that is external to the laboratory instrument, the centralized database having a higher capacity persistent storage relative to the local database,
determine the patient sample result data has been stored at the local database for a predetermined time from generation, and
transmit the patient sample result data to the centralized database responsive to the patient sample result data having been stored at the local database for the predetermined time from generation.

2. The laboratory instrument apparatus of claim 1, wherein the laboratory processor is configured to transmit to an application server the quality control data upon generation and the patient sample result data after the predetermined time for storage in the centralized database, the application server being communicatively coupled to the remotely located centralized database.

3. The laboratory instrument apparatus of claim 2, wherein the laboratory processor is configured to transmit to the application server an indication message indicative that the patient sample result data was generated and locally stored.

4. The laboratory instrument apparatus of claim 3, wherein the laboratory processor is configured to:
receive a request message from the application server, the request message including at least some information from the indication message including an identification of the patient sample result data;
search the local database for the patient sample result data stored among the plurality of other patient sample result data; and
transmit the patient sample result data to the application server.

5. The laboratory instrument apparatus of claim 3, wherein the indication message includes at least one of an identifier of the patient, an identifier of an analysis performed by the laboratory, analyzer, a time of the analysis performed by the laboratory analyzer, an identifier of the laboratory analyzer that performed the analysis, an identifier of the biological sample, and a summary of the analysis performed by the laboratory analyzer.

6. The laboratory instrument apparatus of claim 1, wherein the laboratory processor is configured to:
determine a quantity of laboratory supplies available to the laboratory analyzer and an estimated time a laboratory supply will be exhausted;
determine at least one laboratory supply will be exhausted within a second predetermined time; and
transmit a message including information indicative of the at least one laboratory supply that will be exhausted and a time the at least one laboratory supply will be exhausted.

7. The laboratory instrument apparatus of claim 1, wherein the laboratory processor is configured to:
receive an order for the laboratory analyzer to perform the analysis on the biological sample;
determine an amount of a chemical supply needed by the laboratory analyzer to perform the analysis in conjunction with other ordered analyses that have not been performed; and
conditioned on the amount of the chemical supply needed being greater than a current supply, transmit a message to the application server requesting additional chemical supply before the analysis is performed.

8. The laboratory instrument apparatus of claim 1, wherein the predetermined time is 30 days.

9. The laboratory instrument apparatus of claim 1, wherein the laboratory processor is configured to receive from a second laboratory analyzer second patient sample result data based on a second different analysis on a second biological sample from the patient,
wherein the local database is configured to locally store the second patient sample result data among other patient sample result data associated with the second laboratory analyzer.

10. A laboratory instrument apparatus comprising:
a laboratory analyzer configured to receive a biological sample from a patient and a control biological sample and configured to perform one or more tests comprising an analysis on the biological sample and an analysis on the control biological sample;

a laboratory processor of the laboratory instrument apparatus configured to receive from the laboratory analyzer both patient sample result data based on the analysis on the biological sample from the patient, and quality control data based on the analysis on the control biological sample, the quality control data being indicative of an accuracy or performance of the laboratory instrument apparatus or a specific test of the one or more tests performed by the laboratory analyzer; and a local database configured to locally store the patient sample result data among a plurality of other patient sample result data, the local database being located on the laboratory instrument apparatus;

wherein the laboratory processor is configured to operate in conjunction with the laboratory analyzer to:
- determine whether data generated by the laboratory analyzer comprises the patient sample result data or the quality control data,
- conditioned on the generated data comprising the patient sample result data, store the patient sample result data on the local database,
- conditioned on the generated data comprising the quality control data, transmit the quality control data to be stored in a centralized database that is external to the laboratory instrument, the centralized database having a higher capacity persistent storage relative to the local database,
- determine the patient sample result data has been stored at the local database for a predetermined time from generation, and
- transmit the patient sample result data to the centralized database responsive to the patient sample result data having been stored at the local database for the predetermined time from generation;

wherein the laboratory processor is configured to transmit to an application server the quality control data upon generation and the patient sample result data after the predetermined time for storage in the centralized database and an indication message indicative that the patient sample result data was generated and locally stored, the application server being communicatively coupled to the remotely located centralized database;

wherein the laboratory processor is configured to:
- receive a request message broadcast from the application server, the request message including at least some information from the indication message including an identification of a laboratory analyzer type;
- determine the laboratory analyzer is of the laboratory analyzer type that was identified in the request message;
- instruct the laboratory analyzer to generate the quality control data by performing the analysis on the control biological sample responsive to receiving the broadcast message; and
- transmit the generated quality control data to the application server.

* * * * *